United States Patent [19]

Barkyoumb et al.

[11] Patent Number: 5,586,824

[45] Date of Patent: Dec. 24, 1996

[54] METHOD OF MEASURING THE THERMAL CONDUCTIVITY OF MICROSCOPIC GRAPHITE FIBERS

[75] Inventors: John Barkyoumb, Beltsville; Lawrence T. Kabacoff, Columbia; David J. Land, Silver Spring, all of Md.

[73] Assignee: The United States of America as represented by the Secretary of the Navy, Washington, D.C.

[21] Appl. No.: 260,273

[22] Filed: Jun. 14, 1994

[51] Int. Cl.$^6$ ................................................ G01N 25/18
[52] U.S. Cl. .............................................. 374/44; 73/159
[58] Field of Search ............................ 374/5, 7, 44, 45; 73/159, 160; 356/432

[56] References Cited

U.S. PATENT DOCUMENTS

| | | | |
|---|---|---|---|
| 4,468,136 | 8/1984 | Murphy et al. | 374/45 |
| 4,522,510 | 6/1985 | Rosencwaig et al. | 374/7 |
| 4,589,783 | 5/1986 | Thomas et al. | 374/45 |
| 4,666,308 | 5/1987 | Williams | 356/432 |
| 4,872,743 | 10/1989 | Baba et al. | 350/353 |
| 5,591,272 | 5/1996 | Morris et al. | 374/45 |

FOREIGN PATENT DOCUMENTS

| | | | |
|---|---|---|---|
| 1721492 | 3/1992 | U.S.S.R. | 374/44 |
| 1820308 | 6/1993 | U.S.S.R. | 374/44 |
| 93/03352 | 2/1993 | WIPO | 374/44 |

OTHER PUBLICATIONS

W. B. Jackson et al., Photothermal Deflection Spectroscopy and Detection, Applied Optics, vol. 20, No. 8, Apr. 1981.

*Primary Examiner*—William A. Cuchlinski, Jr.
*Assistant Examiner*—Andrew Hirshfeld
*Attorney, Agent, or Firm*—John Forrest; Roger D. Johnson

[57] ABSTRACT

A metal or graphite fiber is suspended in a working fluid having a high refractive index change with the temperature and a modulated laser beam heats the fiber producing a synchronous thermal wave in the fiber whose amplitude and phase are measured by passing a probe laser beam through the liquid close to the fiber and converting the probe beam deflections into an electric signal. A theoretical model of the thermal wave is used to calculate the amplitude and phase shift of a theoretical thermal wave for points along the fiber from physical characteristics of the lasers and the fiber including an estimate of the thermal conductivity of the fiber. The straight line slope of the log amplitude or of the phase shift of the theoretical wave versus distance is compare against the straight line slope of the log amplitude or the phase shift versus distance for the electrical signal and the estimated value for the thermal conductivity of the fiber is adjusted until the theoretical slope and the electrical signal slope are the same which means that the thermal conductivity of the fiber has been found.

18 Claims, 3 Drawing Sheets

METHOD OF MEASURING THE THERMAL CONDUCTIVITY OF MICROSCOPIC GRAPHITE FIBERS

BACKGROUND OF THE INVENTION

This invention relates to graphite materials and more particularly to graphite fibers. High thermal and electrical conductivity graphite fibers are being investigated and tested for suitability in applications such as electronic packaging and space-based panels and structural components. The efficacy of the fibers and fiber-based composites for thermal management is directly proportional to the thermal conductivity (or thermal diffusivity) of the fibers. The magnitude of the thermal diffusivity is related to the orientation of the graphite planes along the fiber axis, crystalline grain size, and other similar material parameters. The electrical conductivity of these fibers can be measured and the thermal conductivity of bulk composites can be measured, but currently there does not exist the ability to measure the thermal conductivity of individual fibers, especially with a means that is suitable for the factory floor.

SUMMARY OF THE INVENTION

An object of this invention is to provide a new method of measuring the thermal conductivity and thermal diffusivity of an individual small metal or graphite fiber.

Another object of this invention is to provide a nondestructive method of measuring the thermal conductivity and thermal diffusivity of an individual small metal or graphite fiber.

These and other objects of this invention are achieved by providing a method of measuring the thermal conductivity in a graphite or metal fiber by suspending the fiber in a working fluid having a high refractive index change with temperature;

heating the fiber at a first point by means of a modulated pump laser beam;

passing a weak continuous intensity probe laser beam through the working fluid close to a second point on the fiber so that the deflection of the probe laser beam is a measure of the amplitude and phase shift of a synchronous thermal wave passing through the second point as a result of the heating of the fiber by the modulated pump laser beam;

converting the probe laser beam deflection into an electrical signal whose amplitude and phase shift correspond to the amplitude and phase shift of the synchronous thermal wave as it passes through the second point;

recording either the maximum or the RMS amplitude and the phase shift of the electrical signal and the distance between the first point (pump laser beam) and the second point (probe laser beam);

increasing the distance between the first point (pump laser beam) and the second point (probe laser beam) and repeating the measurements and continuing this procedure until a desired number of points have been measured:

obtaining the straight line slope of the plot of the logarithm of the amplitude of the electrical signal versus the distance between first point and the second point;

obtaining the straight line slope of the plot of the phase shift of the electrical signal versus the distance between the first point and the second point. This completes the experimental part of the process.

In the theoretical part, a mathematical model for the synchronous thermal wave produced in a uniform cylindrical fiber by a modulated pump laser beam is used to calculate either the theoretical maximum amplitude or the theoretical phase shift of the synchronous thermal wave at a number of points from inputs which include the modulation frequency of the pump laser beam, the offset of the probe laser beam from the fiber, and the density, specific heat, and diameter of the sample fiber, and the distance of each point from the pump laser beam, and finally an initial estimate of the thermal conductivity. If the maximum amplitude is calculated, the slope of the logarithm of the maximum amplitude versus distance from the pump laser beam is calculated and then compared to the slope of the logarithm of the experimentally measured electrical signal amplitude versus the distance between the pump and probe laser beams which was determined above. If the phase shift is calculated, the slope of the calculated phase shift versus the distance from the pump laser beam is calculated and compared to the experimentally measured (determined) slope of the electrical signal phase shift versus the distance between the pump and probe laser beams which was determined above. The value of the thermal conductivity input is changed to bring the calculated slope (log amplitude or phase shift) closer to the corresponding measured electrical signal slope (log amplitude or phase shift) and the calculations are repeated. This is continued until the slopes are the same which means that the correct value for the thermal conductivity was used. While the thermal conductivity can be determined from the amplitude alone or the phase shift alone, it is preferable to determine it by both methods and compare the results as a check. Widely different results would indicate a problem such as improper focus of the pump laser beam on the fiber or too low a fiber thermal conductivity for this method to be used.

BRIEF DESCRIPTION OF DRAWINGS

A more complete understanding of the invention and many of the attendant advantages thereof will be readily appreciated as the same become better understood by reference to the following detailed description when considered in connection with the accompanying drawings wherein.

DETAILED DESCRIPTION OF THE PREFERRED EMBODIMENT

Figure 1:
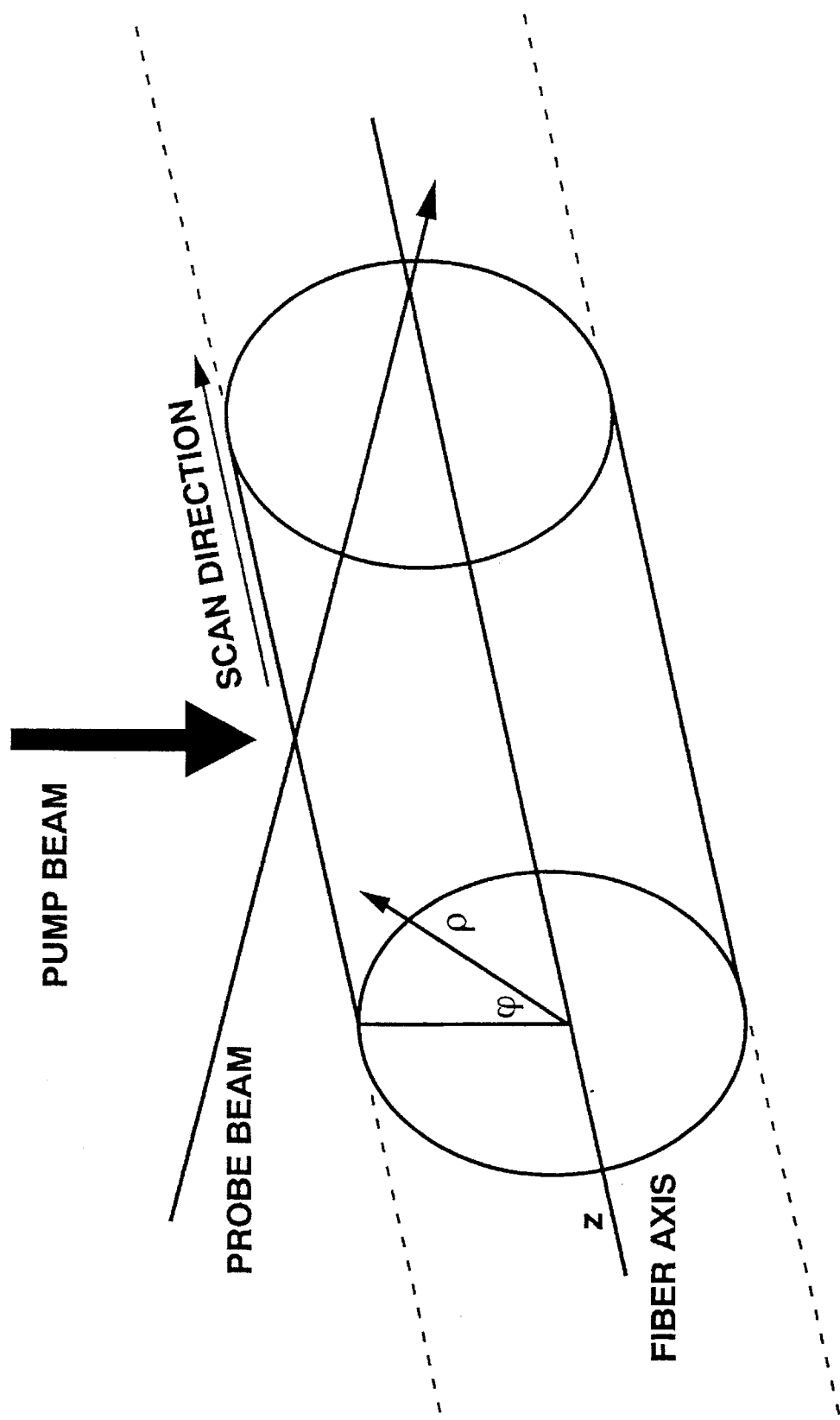
FIG. 1 is a schematic illustrating the orientation of the fiber being tested, the pump laser beam, and the probe laser beam.

The method of the present invention uses a modification of the optical pump-probe technique known as Transverse Photothermal Deflection (or mirage effect) to measure the thermal diffusivity of small cylindrical samples such as wires or fibers. Typical sample diameters are from 5 to 100 µm. Previously, this method had only been developed for flat planar samples such as thin films and bulk samples. The photothermal deflection method uses one laser beam, typically a moderately high power continuous wave (cw) Ar-ion laser focused onto the sample, as the heat source. This beam is modulated at low frequencies (<200 Hz) by a beam chopper to produce a synchronous thermal wave that diffuses along the sample and into the surrounding medium. Preferably the pump laser beam is modulated at a frequency of from 20 to less than 200 Hz and more preferably at from 20 to 100 Hz. A weak He-Ne laser is directed perpendicular to the fiber so as to just graze the sample surface. This probe laser beam is deflected by the temperature gradient in the fluid medium immediately adjacent to the sample surface. By varying the separation between the pump and probe beams, one can measure the temperature gradient at the surface of the sample as a function of distance along the sample. From this information on the temperature gradient along the sample, the thermal diffusivity and thermal conductivity of the sample can be determined. The information on the temperature gradient is in the form of the amplitude of the photothermal and also the phase shift of the synchronous thermal wave along the fiber. A plot of the logarithm of the amplitude versus the separation between the pump and probe beams becomes a straight line after the separation exceeds a small distance (<1 mm). The slope of this line is used to determine the diffusivity and conductivity of the fiber. Similarly, a plot of the phase shift of the wave versus the separation between the pump and probe beams becomes a straight line after the separation exceeds a small amount (<1 mm). The slope of this line is also used to determine the diffusivity and conductivity of the fiber.

Next the thermal conductivity of the fiber is determined by using a mathematical model of the temperature gradient along the fiber being heated by the modulated pump laser beam. The mathematical model is used to calculate the maximum amplitude and the phase shift of a theoretical thermal wave at each of a number of points on the fiber. The mathematical model uses inputs that include the modulation frequency of the pump laser beam and the offset of the probe beam from the fiber in the experimental measurements, and also the actual density, specific heat, and diameter of the sample fiber being measured. The mathematical model also needs an initial estimate of the thermal conductivity of the sample fiber. In method 1, the slope of the log of the amplitude of the thermal wave versus distance from the pump laser beam is calculated and compared with the experimental slope of the logarithm of the electrical signal amplitude versus distance between the pump and probe laser beams. The value of the thermal conductivity is changed to bring the calculated slope closer to the experimentally determined (electrical signal) slope and the process is repeated until the slopes are the same. The value of the thermal conductivity (based on amplitude) has then been determined. In the second method, the slope of the phase shift of the thermal wave versus distance from the pump laser beam is calculated and compared to the experimentally determined slope of the phase shift of the electrical signal versus the distance between the pump and the probe laser beams. The value of the thermal conductivity is changed to bring the calculated phase shift slope closer to the experimentally measured (electrical signal) phase shift slope. This procedure is repeated until the slopes are the same. The value of the thermal conductivity of the fiber (based on phase shift) has then been determined. If both methods are used, the results can be compared as a check that the pump beam was properly focused on the fiber and that the thermal conductivity was sufficiently high for this procedure to be used. Widely divergent results indicate that something is wrong.

FIG. 1 illustrates that the fiber axis, probe beam, and pump beam are perpendicular to each other. It also illustrates that the system can be represented in cylindrical coordinates.

Figure 2:
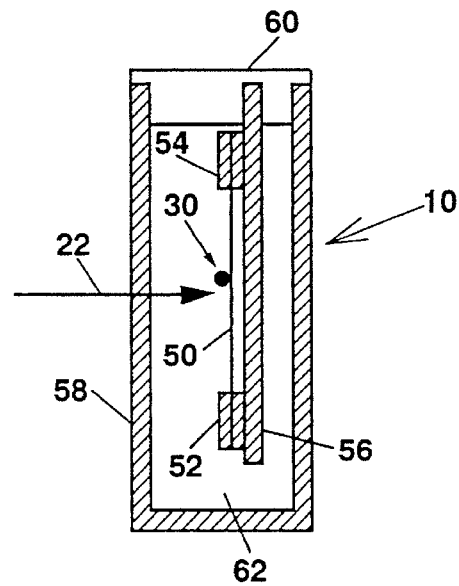
FIG. 2 is a sectional side view of the optical cuvette into which the test fiber is mounted on a standoff slide.
Figure 3:
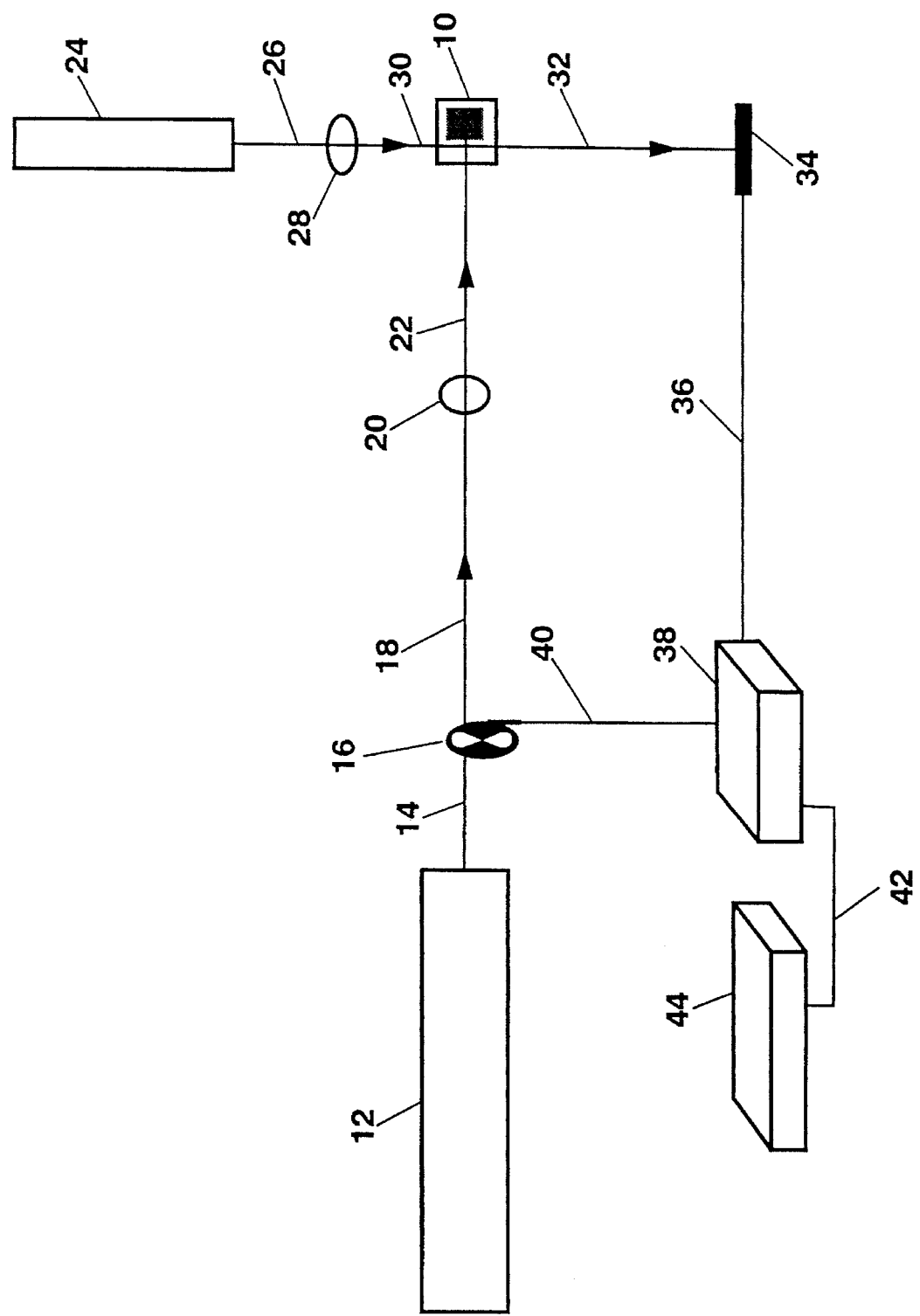
FIG. 3 is a schematic diagram of the overall arrangement of the test equipment.

FIGS. 2 and 3 are schematic drawings which illustrate the equipment set up for the experimental part of the present procedure. FIG. 2 shows the sample cell assembly 10 and its relationship to the modulated pump laser beam 22 and probe beam 26. The sample fiber 50 is mounted by means of glass standoffs 52 and 54 which are attach to glass slide 56. The glass slide 56 is supported inside of a glass cuvette 58 by means of a stopper 60 which closes the open end of the cuvette 58. The cuvetted 58 is filled with a working fluid 62 which has a high refractive index change with temperature. Preferred working fluids include n-pentane, methanol, and carbon tetrachloride, with carbon tetrachloride being most preferred. Carbon tetrachloride has a refractive index change with temperature that is about 100 times that of air. Also shown in FIG. 2 are the pump laser beam 22 and the modulated probe laser beam 30. The modulated pump laser beam 22 is focused on the sample fiber 50 and is perpendicular to the axis of the sample fiber 50. The probe laser beam 30 is shown coming out of the paper and is perpendicular to both the axis of the sample fiber 50 and the pump beam 22. The probe laser beam 30 grazes the sample fiber 50, passing within 50 to 100 µm of the surface of the sample fiber 50.

FIG. 3 is a schematic of a typical arrangement of apparatus used in the experimental part of the present method. A continuous wave (cw) pump laser 12 puts out a cw laser beam 14 which is modulated by a beam chopper 16 to product a synchronous laser beam 18 which is focused by a focusing lens 20 and the resulting modulated, focused pump laser beam 22 is projected on to the sample fiber 50 as shown in FIG. 2. The modulated, focused pump laser beam 22 is centered on the sample fiber 50. This centering can be determined by observing the diffraction pattern of the pump beam by the cylindrical sample fiber for sample diameters less than or approximately equal to 100 µm. The pump laser beam 22 is perpendicular to the axis of the sample fiber 50 and is used to heat the sample fiber 50. Referring again to FIG. 3, there is shown a probe laser 24 which produces a weak continuous intensity laser beam 26 which is focused by focusing lens 28 and the resulting focused probe laser beam 30 grazes (within 50 to 100 µm) the surface of the sample fiber 50 as shown in FIG. 2. The point where the probe beam offset is zero can be found by observing the diffraction pattern of the probe beam from the cylindrical sample fiber (or wire). Note that the temperature of the sample fiber 50 at any point is not constant but rather oscillates at a frequency corresponding to beam chopper 16 frequency. The sample fiber 50 heats the working fluid 62 nearby causing the index of refractive index of the working fluid 62 to change proportionately which in turn causes the probe beam 30 to deflect proportionately. Thus the deflection of the probe beam 30 is continuously changing as the temperature of the sample fiber 50 at that point is continuously changing. Referring again to FIG. 3, the continuously changing deflected probe beam 32 comes out of the sample cell array 10 and is projected onto a position-sensitive detector 34. The output 36 of the position-sensitive detector 34 is an amplified electrical signal whose magnitude is proportional to the deflection of the probe laser beam 30 and thus the temperature of the fiber at the point being measured. The output 36 of the position detector 34 and a signal reference 40 from the beam chopper 16 are both sent to a lock-in amplifier 38 which calculates the amplitude and phase of the electrical signal output 36 of the position-sensitive detector 34. The amplitude and phase information is sent from the lock-in amplifier 38 via line 42 to a computer 44.

The following specific equipment and procedures were used in the experiments. Referring to FIG. 3, the probe beam source was an intensity-stabilized He-Ne laser 24. This probe beam 26 was focused with a 75 mm focal length lons 28 to a beam 30 having a diameter of approximately 50 μm at the closest approach to the wire or fiber surface. The pump laser 12 was a cw argon-ion operating at 488 nm with a beam power of between 100 and 500 mW focused to a Gaussian $1/e^2$ diameter of approximately 30 μm at the sample surface. A standard 50% duty-cycle optical beam chopper 16 was inserted in the pump beam path to modulate the beam.

Referring to FIG. 2, a short length (about 1 cm) of the sample fiber 50 to be investigated was mounted vertically under slight tension in an optical cuvette 58 on glass standoffs 52 and 54 on a glass slide 56. The optical cuvette 58 was filled with carbon tetrachloride, $CCl_4$, as the working fluid because of its high refractive index change with temperature which allows low pump laser powers to be used. This also kept the temperature of the fiber low, at least below the boiling point of $CCl_4$ at 77° C. The deflection of the probe beam 32 was measured with a Hamamatsu model S1200 2-dimensional silicon PIN photodiode position-sensitive detector 34. (These detectors are also known as 2-d lateral cells.) The amplified output 36 of the position-sensitive detector 36 was sent to a lock-in amplifier 38 where it was referenced to the chopped light 18 of the pump laser. The amplitude and phase of the signal can then be read from the lock-in using standard phase-sensitive detection techniques. The sample cell is mounted on a rotation stage and an x-y-z micrometer-driven translation stage with a precision of ±1 μm. The sample cell is also on a kinematic base to adjust the angle the same makes with the vertical along two axes of rotation. The distance from the sample cell to the detector is roughly 15 cm.

The pump beam is translated relative to the probe beam and sample using an arrangement of mirrors and computer-controlled micropositioners that allow the focused pump beam to move along the fiber axis while maintaining normal incidence with respect to the fiber axis. The data collection process involves stepping the pump beam position along the axis of the cylindrical sample at a fixed offset in ≈50–100 μm steps from the zero point and measuring the phase and amplitude of the beam deflection at each point. The zero point is the point where the pump laser beam and the probe laser beam initially intersect. The zero point is determined by maximizing the photothermal deflection signal on the photodiode position-sensitive detector as the pump laser beam position is varied.

To obtain an expression for the observed photothermal signal, one needs to find the temperature (or temperature gradient) of the sample and surrounding medium as a function of position. Secondly, the propagation of the probe beam in the resulting temperature gradient in the sample and medium must be determined.

Consider a uniform cylindrical wire (or fiber) of radius a that is heated by a sinusoidally modulated laser beam of power P incident on the sample normal to the sample's long axis as shown in FIG. 1. Assuming a Gaussian intensity profile with a $1/e^2$ radius of R for the pump laser beam, the heat absorbed by the cylinder per unit volume per unit time $Q(\rho,\phi,z,t)$ can be expressed by $$Q(\rho, \phi, z, t) = \qquad\qquad (1)$$

$$P\beta(\phi)\{1 - R(\phi)\}e^{-\beta(\phi)(a-\rho)}\frac{2e^{-2(z^2+a^2\sin^2\phi)/R^2}}{\pi R^2} \cdot \frac{1}{2}(1 + e^{-i\omega t})$$

where ω is the angular frequency of the pump beam modulation (chopping), $R(\phi)$ is the reflection coefficient of the wire given by the Fresnel reflection coefficient, and $\beta(\phi)$ is an absorption length that depends on the angle of incidence of the pump beam. The effective angular dependence of the absorption length $\beta(\phi)$ is due to refractive effects that determine the actual path taken by the beam in the sample. For the large absorption coefficients appropriate for metal wires and carbon fibers in the visible, the skin depth is ≈0.1 μm and $\beta(\phi)$ is well approximated by the absorption coefficient α of the material.

The complete solution for the temperature in either the sample or medium as a function of position and time can be expressed by $$T\hat{T}(\rho,\phi,z,t)=T_a+T_{dc}+\hat{T}_{ac}(\rho,\phi,z)e^{-i\omega t} \qquad (2)$$

where $T_a$ is the ambient temperature, $T_{dc}$ is the steady-state temperature rise due to the heating of the sample, and $\hat{T}_{ac}$ is that part of the temperature signal that is oscillating coherently at the pump beam chopping frequency. We are only interested in the sinusoidally oscillating beam deflection and consequently only will consider $\hat{T}(\rho,\phi,z,t)=\hat{T}_{ac}$ in the following. The temperature solution is complex to represent the phase shift in the response of the system with respect to the pump source frequency. Following the work of L. D. Favro et al. in *Photoacoustic and Thermal Wave Phenomena in Semiconductors*, A. Mandelis, ed. New York:Elsevier Chapter 4, pages 69-96, $\hat{T}(\rho,\phi,z,t)$ can be expressed in terms of its Fourier transform:

$$\hat{T}(\rho, \phi, z) = \int_{-\infty}^{\infty} dk e^{ikz}\hat{t}(k, \rho, \phi) \qquad (3)$$

The temperature in the fluid as a function of position along the fiber is given by $$\hat{T}(\rho, \phi, z) = \frac{\alpha P}{2}\sum_{m=0}^{\infty} \hat{q}_m\cos m\phi \int_{-\infty}^{\infty} dk e^{ikz} e^{-k^2R^2/8}A_m(\hat{\delta}_0, \hat{\delta}_1)K_m(\hat{\delta}_0\rho) \qquad (4)$$

where $K_m(\hat{\delta}_0\rho)$ is the $m^{th}$ order modified Bessel's function $q_m$ are the Fourier components of the expansion of the angular dependence of the pump beam and the reflectance of the cylindrical sample. P is the pump beam power. $A_m(\hat{\delta}_0, \hat{\delta}_1)$ is a factor given by the radial boundary conditions at the fiber surface $\rho=a$ where $$A_m(\hat{\delta}_0, \hat{\delta}_1) = \frac{(2/(2\pi)^{3/2})(1/aR)\int_0^a d\rho' \rho' \hat{I}_m(\hat{\delta}_1\rho')e^{-\alpha(a-\rho')}}{\kappa_1\hat{\delta}_1[\partial I_m(\hat{\delta}_1 a)/\partial(\hat{\delta}_1 a)]K_m(\hat{\delta}_0 a) - \kappa_0\hat{\delta}_0[\partial K_m(\hat{\delta}_0 a)/\partial(\hat{\delta}_0 a)]I_m(\hat{\delta}_1 a)} \qquad (5)$$

The parameters $$\hat{\delta}_{\{0,1\}} = \sqrt{k^2 - i\omega/D_{\{0,1\}}}$$

can be considered inverse characteristic thermal diffusion lengths of each Fourier component of the thermal waves in the fluid and sample where $D_{\{0,1\}}$ is the thermal diffusivity of the fluid and sample respectively.

The calculation of the beam deflection from the temperature gradient has been shown previously by L. D. Favro et al., cited above, and the procedure does not differ in our case. For small deflection, the complex normal deflection angle $\theta_n$ is given by $$\hat{\theta}_n \cong \frac{1}{\eta_0} \frac{\partial n}{\partial T} \int_S \nabla_\perp \hat{T}(\rho, \phi, z, t) ds \qquad (6)$$

where $\partial n/\partial T$ is the change in refractive index of the external medium with temperature.

EXAMPLES

To evaluate Equation 4, we used standard FFT routines for the Fourier transforms and explicitly evaluated terms of order m in the expansion of Equation 4 to obtain the contribution from each term. The infinitely narrow beam deflection $\theta_n(\rho, \phi z)$ was then evaluated at various positions $\rho$ and $z$ in order to numerically integrate Equation 5 along the path S and to simulate the effect of a finite-width probe beam. The finite-width of the probe beam has no effect on the measured thermal conductivity by this method.

Photothermal deflection measurements were made on samples of gold, tungsten, copper, and nickel wires with diameters between 15 and 100 μm to test the theory. The measurements were made varying the chopping frequencies, probe beam offset, and pump power to verify the theoretical photothermal deflection equations. Electrical resistance measurements were also made on the wires and the thermal conductivity was determined from the electrical conductivity using the Wiedemann-Franz law. These results are presented in Table 1. The values for the thermal conductivity derived from the electrical measurements differed from those obtained from the photothermal measurements by no more than 10% with the exception of the nickel wires. This technique works less well on low conductivity samples, such as nickel, as the signal dies out faster with distance along the wire resulting in more error in the measurements.

TABLE 1

| Material | wire dia. | $K_{el}$ W/m − K | parameter measured | $k_{PT}$ (W/m − K) | $D_{PT}$ (cm²/S) |
|---|---|---|---|---|---|
| gold | 50 μm | 323 ± 27 | amplitude phase | 287 ± 12 289 ± 12 | 1.15 ± 0.04 1.16 ± 0.04 |
| copper | 50 μm | 405 ± 29 | amplitude phase | 379 ± 17 389 ± 15 | 1.10 ± 0.05 1.12 ± 0.04 |
| nickel | 50 μm | 100 ± 7 | amplitude phase | 93 ± 10 77 ± 6 | 0.24 ± 0.03 0.19 ± 0.02 |
| tungsten | 100 μm | 158 ± 7 | amplitude phase | 160 ± 10 162 ± 10 | 0.62 ± 0.06 0.62 ± 0.06 |

Figure 4A:
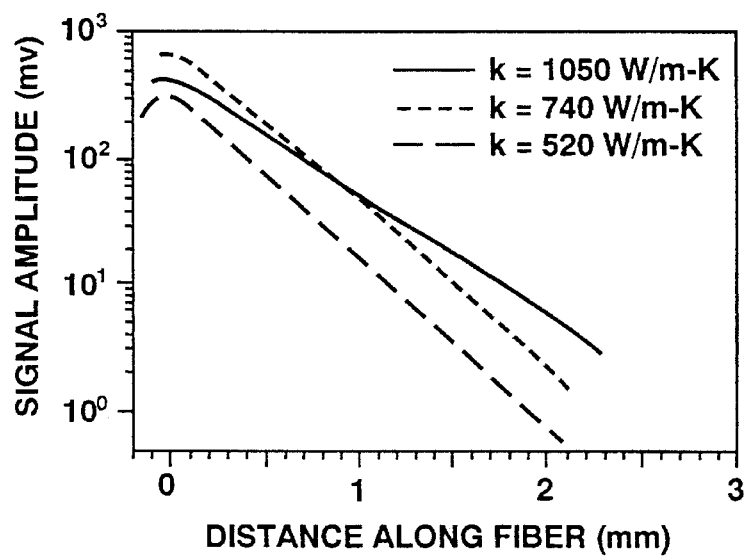
FIG. 4A presents plots of the logarithm of the signal amplitude versus the distance between the pump laser beam (heating) and the probe laser beam (measuring) for three graphite fibers.
Figure 4B:
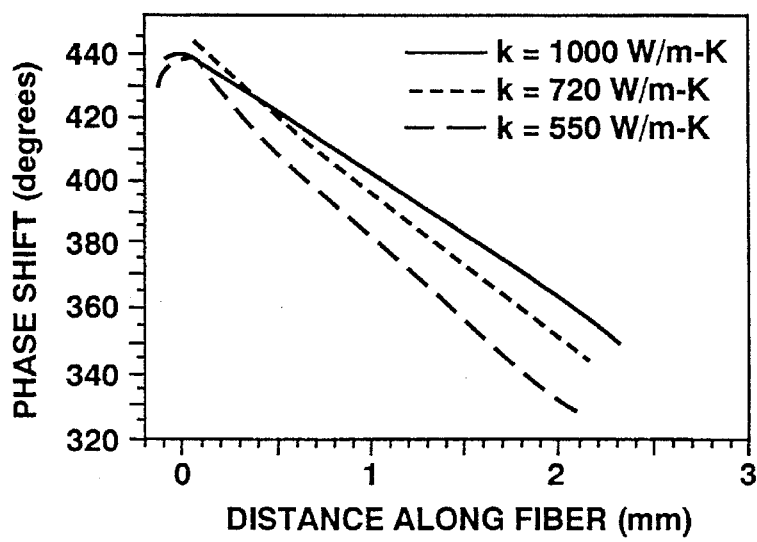
FIG. 4B presents the corresponding plots of the signal phase shifts versus the distance between the pump laser beam and the probe laser beam for the same three graphite fibers.

Amoco Performance Products, Inc. has provided us with samples of different grades of graphite fibers that are optimized for high thermal conductivity. These fibers are of cylindrical cross-section and have a diameter of approximately 10 μm. Shown in FIG. 4A is a plot of the log of the rms amplitude of the photothermal signal as a function of distance along the fiber for three different grades of fibers as the pump beam was stepped along the sample. The probe beam was held at a fixed offset of 50 to 100 μm from the fiber during the measurement. FIG. 4B is a plot of the phase shift (in degrees) of the photothermal signal relative to the pump beam as a function of distance for the same fiber samples as in FIG. 4A. The origin of the distance axis is the point where the pump and probe beams coincide at z=0. The rate of change (slope) of both the photothermal signal and its phase shift as a function of distance z along the fiber is quite sensitive to the thermal diffusivity of the fiber. Intuitively, one would expect the signal to fall off more slowly (in roughly an exponential fashion) with distance for high-conductivity fibers than for low conductivity fibers. The phase shift shows the same trend.

The diffusivity was obtained from the data as shown in FIGS. 4A and 4B by measuring the slope of the photothermal signal or phase shift as a function of distance between 0.5 and 3 mm from z=0 where the pump and probe beam coincide. The theoretical slope was calculated using Equations 4-6 and a Newton-Raphson search routine varying the diffusivity until the predictedslope matches the experimental slope. The results are summarized in table 2.

TABLE 2

| GRAPHITE SAMPLE | FIBER DIAMETER | PARAMETER MEASURED | $k_{pt}$ (W/M − k) |
|---|---|---|---|
| 1 | 10 μm | amplitude phase | 1,050 1,000 |
| 2 | 10 μm | amplitude phase | 740 720 |
| 3 | 10 μm | amplitude phase | 520 550 |

```
      PROGRAM TPDS7
C
C THIS PROGRAM USES ROUTINES CFFTI, CFFTB1, CFFTB, CFFTI1, PASSB5
C PASSB4, PASSB3, PASSB2, PASSB FROM THE NETLIB PUBLIC DOMAIN
C FFTPACK ROUTINES.  THESE ROUTINES ARE LISTED IN THE PROGRAM AND
C MUST BE COMPILED WITH THE PROGRAM.  THERE ARE NO OTHER DEPENDENCIES
C IN THIS PROGRAM
C THIS PROGRAM USES POLYNOMIAL COEFF. FOR THE BESSEL FUNCTIONS FROM
C ABRAMOWITZ AND STEGUN, NBS APPLIED MATH SERIES #55, (DOVER, 1965).
C THESE POLYNOMIAL FITS ARE ONLY VALID FOR ARGUMENTS OF THE BESSEL
C FUNCTIONS FROM 0 TO 3.  THIS IS SUFFICIENT FOR THIS PROGRAM BUT
C SHOULD NOT BE USED BEYOND THE RANGE OF VALIDITY.
C THE BESSEL FUNCTIONS ARE EVALUATED IN ROUTINES CBESJ, CBESY, CBESZ
C
C THE PROGRAM USES A SIMPLE NEWTON'S METHOD FOR FINDING THE
C CONDUCTIVITY
C AND LOOPS WITH A NEW ESTIMATE OF THE THERMAL CONDUCTIVITY
C AT STATEMENT
C LABEL 500
C
      IMPLICIT REAL*4(A-H,O-Z)
      REAL*4 Xmin,Xmax,kappa_0,kappa_1,r,a,freq,D0,D1,delta
```

```
        REAL*4 MSLOPE,PSLOPE,TPSLOPE,TMSLOPE
        COMPLEX delta0,delta1,sigma0,sigma1,MAG,PHASE
        COMPLEX J0,J1,H0,H1,H1R
        COMPLEX GAMMA,GX,GK,dummy
        DIMENSION X(512),q(512),delta0(512),delta1(512)
        DIMENSION J0(512),J1(512),H0(512),H1(512),H1R(512),W(600)
        DIMENSION GAMMA(512),GX(512),GK(512),MAG(512),PHASE(512)

DATA PI /3.14159265359/

C refractive index gradient for CCl4
        dndT = 6.85e-5
        kappa_0 = 1.036e-03

C REQUEST INPUT PARAMETERS
        WRITE(*,1)
   1    FORMAT(1X, 'Frequency of pump beam chopping (Hz):')
        READ(*,*) freq
        WRITE(*,2)
   2    FORMAT(1X,'specific heat (J/g-K):')
        READ(*,*) heat
        WRITE(*,3)
   3    FORMAT(1X,'density (g/cm^3):')
        READ(*,*) rho
        WRITE(*,4)
   4    FORMAT(1X,'diameter of sample (microns):')
        READ(*,*) a
        WRITE(*,5)
   5    FORMAT(1X,'distance of probe beam from center of sample:')
        READ(*,*) r
        WRITE(*,6)
   6    FORMAT(1X,'initial estimate of the thermal conductivity:')
        READ(*,*) kappa_1
        WRITE(*,7)
   7    FORMAT(1X,'measured slope of the phase:')
        READ(*,*) MSLOPE
        WRITE(*,8)
   8    FORMAT(1X,'measured slope of the log of the amplitude:')
        READ(*,*) PSLOPE
        r = 0.5*r*1e-4
        a = 0.5*a*1e-4
        NN = 512
        Xmin = 0.0
        Xmax = 1.2
        delta = (Xmax-Xmin)/(NN-1)

D0 = 7.646e-4
C  THIS IS THE RETURN POINT FOR THE ITERATIVE NEWTON'S SEARCH
    500 D1 = kappa_1/(rho*heat)
```

```
          sigma0 = CMPLX(0,2*PI*freq/D0)
          sigma1 = CMPLX(0,2*PI*freq/D1)
          DO 100 i=1,NN
             x(i) = Xmin + (i-1)*delta
             q(i) = -pi/delta + (i-1)*(2*pi/(delta*NN))
             delta0(i) = CDSQRT(sigma0 - q(i)*q(i))
             delta1(i) = CDSQRT(sigma1 - q(i)*q(i))
             CALL CBESJ(delta1(i)*a,J0(i),J1(i))
             CALL CBESH(delta0(i)*a,H0(i),H1(i))
             CALL CBESH(delta0(i)*r,dummy,H1R(i))
             GAMMA(i) = J0(i)/(kappa_1*delta1(i)*J1(i)*H0(i)
     2              -kappa_0*delta0(i)*J0(i)*H1(i))
             GAMMA(i) = GAMMA(i)/(2*PI)
             GK(i) = dndT*delta0(i)*GAMMA(i)*H1R(i)
             GX(i) = GK(i)
      100 CONTINUE
    C  Call Fourier transforms
          CALL CFFTI (NN,W)
          CALL CFFTB (NN,GX,W)
          DO 110 i=1,NN
             MAG(i)= CABS(GX(i))
             PHASE(i) = ATAN(IMAG(GX(i))/REAL(GX(i)))
      110 CONTINUE C THEORETICAL SLOPES
          TMSLOPE=(LOG(MAG(25))-LOG(MAG(20)))/(X(25)-X(20))
          TPSLOPE=(PHASE(25)-PHASE(20))/(X(25)-X(20))

C CALCULATE THE SLOPE OF THE PHASE FOR ITERATIVE SEARCH
    C RETURN TO LABEL 500 AT BEGINNING OF PROGRAM IF CONVERGENCE NOT MET
          FPRIME = -0.5*PSLOPE/kappa_1
          DIFF = (PSLOPE-TPSLOPE)/FPRIME
    C TEST FOR CONVERGENCE, WRITE ANSWER, AND LOOP OF NECESSARY
          IF (ABS(DIFF) .GT. 1E-2) THEN
             kappa_1 = kappa_1 + DIFF
             WRITE(*,*) kappa_1,DIFF
             GOTO 500
          END IF
          WRITE(*,*) kappa_1,DIFF
          END

SUBROUTINE CBESJ(Z,J0,J1)

COMPLEX Z
          COMPLEX U,J0,J1
          DIMENSION A(6),B(6)
          DATA A /-2.2499997, 1.2656208, -0.3163866, 0.0444479,
     -0.0039444,
     2            0.0002100/
```

```
      DATA B /-0.56249985, 0.21093573, -0.03954289, 0.00443319,
     2      -0.00031761, 0.00001109/
      U=Z/3.0
      J0 = 1+U*U*(A(1)+U*U*(A(2)+U*U*(A(3))
     2      +U*U*(A(4)+U*U*(A(5)+U*U*(A(6))))))
      J1 = 0.5+U*U*(B(1)+U*U*(B(2)+U*U*(B(3))+U*U*(B(4)+U*U*(B(5)
     2      +U*U*(B(6))))))
      J1 = J1*Z
      END

SUBROUTINE CBESY(Z,Y0,Y1)

COMPLEX Z
      COMPLEX U,Y0,Y1,J0,J1
      DIMENSION A(6),B(6)
      DATA PI /3.14159265359/
      DATA A /0.60559366, -0.74350384, 0.25300117, -0.04261214,
     2      0.00427916, -0.00024846/

DATA B /0.2212091, 2.1682709, -1.3164827, 0.3123951,
     2      -0.0400976, 0.0027873/
      U=Z/3.0
      CALL CBESJ(Z,J0,J1)
      Y0 = (2.0/PI)*LOG(Z/2.0)*J0 +0.36746691 + U*U*(A(1)
     2      + U*U*(A(2)+U*U*(A(3))+U*U*(A(4)+U*U*(A(5)+U*U*(A(6))))))
      Y1 = (2.0/PI)*LOG(Z/2.0)*J1 -0.6366198 + U*U*(B(1)
     2      + U*U*(B(2)+U*U*(B(3))+U*U*(B(4)+U*U*(B(5)+U*U*(B(6))))))
      Y1 = Y1/Z
      END

SUBROUTINE CBESH(Z,H0,H1)

COMPLEX Z
      COMPLEX J0,J1,Y0,Y1,H0,H1
      CALL CBESJ(Z,J0,J1)
      CALL CBESY(Z,Y0,Y1)
      H0 = CMPLX(J0,Y0)
      H1 = CMPLX(J1,Y1)
      END
```

```
            SUBROUTINE CFFTI (N,WSAVE)
            DIMENSION        WSAVE(1)
            IF (N .EQ. 1) RETURN
            IW1 = N+N+1
 5          IW2 = IW1+N+N
            CALL CFFTI1 (N,WSAVE(IW1),WSAVE(IW2))
            RETURN
            END

SUBROUTINE CFFTB (N,C,WSAVE)
10          DIMENSION       C(1)         ,WSAVE(1)
            IF (N .EQ. 1) RETURN
            IW1 = N+N+1
            IW2 = IW1+N+N
            CALL CFFTB1 (N,C,WSAVE,WSAVE(IW1),WSAVE(IW2))
15          RETURN
            END

SUBROUTINE CFFTB1 (N,C,CH,WA,IFAC)
            DIMENSION       CH(1)       ,C(1)        ,WA(1)       ,IFAC(1)
            NF = IFAC(2)
20          NA = 0
            L1 = 1
            IW = 1
            DO 116 K1=1,NF
               IP = IFAC(K1+2)
25             L2 = IP*L1
               IDO = N/L2
               IDOT = IDO+IDO
               IDL1 = IDOT*L1
               IF (IP .NE. 4) GO TO 103
30             IX2 = IW+IDOT
               IX3 = IX2+IDOT
               IF (NA .NE. 0) GO TO 101
               CALL PASSB4 (IDOT,L1,C,CH,WA(IW),WA(IX2),WA(IX3))
               GO TO 102
35       101   CALL PASSB4 (IDOT,L1,CH,C,WA(IW),WA(IX2),WA(IX3))
         102   NA = 1-NA
               GO TO 115
         103   IF (IP .NE. 2) GO TO 106
               IF (NA .NE. 0) GO TO 104
40             CALL PASSB2 (IDOT,L1,C,CH,WA(IW))
               GO TO 105
         104   CALL PASSB2 (IDOT,L1,CH,C,WA(IW))
         105   NA = 1-NA
               GO TO 115
45       106   IF (IP .NE. 3) GO TO 109
```

```
            IX2 = IW+IDOT
            IF (NA .NE. 0) GO TO 107
            CALL PASSB3 (IDOT,L1,C,CH,WA(IW),WA(IX2))
            GO TO 108
     107    CALL PASSB3 (IDOT,L1,CH,C,WA(IW),WA(IX2))
     108    NA = 1-NA
            GO TO 115
     109    IF (IP .NE. 5) GO TO 112
            IX2 = IW+IDOT
            IX3 = IX2+IDOT
            IX4 = IX3+IDOT
            IF (NA .NE. 0) GO TO 110
            CALL PASSB5 (IDOT,L1,C,CH,WA(IW),WA(IX2),WA(IX3),WA(IX4))
            GO TO 111
     110    CALL PASSB5 (IDOT,L1,CH,C,WA(IW),WA(IX2),WA(IX3),WA(IX4))
     111    NA = 1-NA
            GO TO 115
     112    IF (NA .NE. 0) GO TO 113
            CALL PASSB (NAC,IDOT,IP,L1,IDL1,C,C,C,CH,CH,WA(IW))
            GO TO 114
     113    CALL PASSB (NAC,IDOT,IP,L1,IDL1,CH,CH,CH,C,C,WA(IW))
     114    IF (NAC .NE. 0) NA = 1-NA
     115    L1 = L2
            IW = IW+(IP-1)*IDOT
     116 CONTINUE
            IF (NA .EQ. 0) RETURN
            N2 = N+N
            DO 117 I=1,N2
               C(I) = CH(I)
     117 CONTINUE
            RETURN
            END

SUBROUTINE CFFTI1 (N,WA,IFAC)
            DIMENSION      WA(1)      ,IFAC(1)      ,NTRYH(4)
            DATA NTRYH(1),NTRYH(2),NTRYH(3),NTRYH(4)/3,4,2,5/
            NL = N
            NF = 0
            J = 0
     101 J = J+1
            IF (J-4) 102,102,103
     102 NTRY = NTRYH(J)
            GO TO 104
     103 NTRY = NTRY+2
     104 NQ = NL/NTRY
            NR = NL-NTRY*NQ
            IF (NR) 101,105,101
     105 NF = NF+1
```

```
            IFAC(NF+2) = NTRY
            NL = NQ
            IF (NTRY .NE. 2) GO TO 107
            IF (NF .EQ. 1) GO TO 107
            DO 106 I=2,NF
               IB = NF-I+2
               IFAC(IB+2) = IFAC(IB+1)
        106 CONTINUE
            IFAC(3) = 2
        107 IF (NL .NE. 1) GO TO 104
            IFAC(1) = N
            IFAC(2) = NF
            TPI = 6.28318530717959
            ARGH = TPI/FLOAT(N)
            I = 2
            L1 = 1
            DO 110 K1=1,NF
               IP = IFAC(K1+2)
               LD = 0
               L2 = L1*IP
               IDO = N/L2
               IDOT = IDO+IDO+2
               IPM = IP-1
               DO 109 J=1,IPM
                  I1 = I
                  WA(I-1) = 1.
                  WA(I) = 0.
                  LD = LD+L1
                  FI = 0.
                  ARGLD = FLOAT(LD)*ARGH
                  DO 108 II=4,IDOT,2
                     I = I+2
                     FI = FI+1.
                     ARG = FI*ARGLD
                     WA(I-1) = COS(ARG)
                     WA(I) = SIN(ARG)
        108       CONTINUE
                  IF (IP .LE. 5) GO TO 109
                  WA(I1-1) = WA(I-1)
                  WA(I1) = WA(I)
        109    CONTINUE
               L1 = L2
        110 CONTINUE
            RETURN
            END

SUBROUTINE PASSB (NAC,IDO,IP,L1,IDL1,CC,C1,C2,CH,CH2,WA)
            DIMENSION      CH(IDO,L1,IP)          ,CC(IDO,IP,L1)
```

```
              1               C1(IDO,L1,IP)         ,WA(1)      ,C2(IDL1,IP),
              2               CH2(IDL1,IP)
        IDOT = IDO/2
        NT = IP*IDL1
        IPP2 = IP+2
        IPPH = (IP+1)/2
        IDP = IP*IDO
C
        IF (IDO .LT. L1) GO TO 106
        DO 103 J=2,IPPH
           JC = IPP2-J
           DO 102 K=1,L1
              DO 101 I=1,IDO
                 CH(I,K,J) = CC(I,J,K)+CC(I,JC,K)
                 CH(I,K,JC) = CC(I,J,K)-CC(I,JC,K)
    101       CONTINUE
    102    CONTINUE
    103 CONTINUE
        DO 105 K=1,L1
           DO 104 I=1,IDO
              CH(I,K,1) = CC(I,1,K)
    104    CONTINUE
    105 CONTINUE
        GO TO 112
    106 DO 109 J=2,IPPH
           JC = IPP2-J
           DO 108 I=1,IDO
              DO 107 K=1,L1
                 CH(I,K,J) = CC(I,J,K)+CC(I,JC,K)
                 CH(I,K,JC) = CC(I,J,K)-CC(I,JC,K)
    107       CONTINUE
    108    CONTINUE
    109 CONTINUE
        DO 111 I=1,IDO
           DO 110 K=1,L1
              CH(I,K,1) = CC(I,1,K)
    110    CONTINUE
    111 CONTINUE
    112 IDL = 2-IDO
        INC = 0
        DO 116 L=2,IPPH
           LC = IPP2-L
           IDL = IDL+IDO
           DO 113 IK=1,IDL1
              C2(IK,L) = CH2(IK,1)+WA(IDL-1)*CH2(IK,2)
              C2(IK,LC) = WA(IDL)*CH2(IK,IP)
    113    CONTINUE
           IDLJ = IDL
           INC = INC+IDO
```

```
            DO 115 J=3,IPPH
               JC = IPP2-J
               IDLJ = IDLJ+INC
               IF (IDLJ .GT. IDP) IDLJ = IDLJ-IDP
               WAR = WA(IDLJ-1)
               WAI = WA(IDLJ)
               DO 114 IK=1,IDL1
                  C2(IK,L) = C2(IK,L)+WAR*CH2(IK,J)
                  C2(IK,LC) = C2(IK,LC)+WAI*CH2(IK,JC)
114            CONTINUE
115         CONTINUE
116      CONTINUE
         DO 118 J=2,IPPH
            DO 117 IK=1,IDL1
               CH2(IK,1) = CH2(IK,1)+CH2(IK,J)
117         CONTINUE
118      CONTINUE
         DO 120 J=2,IPPH
            JC = IPP2-J
            DO 119 IK=2,IDL1,2
               CH2(IK-1,J) = C2(IK-1,J)-C2(IK,JC)
               CH2(IK-1,JC) = C2(IK-1,J)+C2(IK,JC)
               CH2(IK,J) = C2(IK,J)+C2(IK-1,JC)
               CH2(IK,JC) = C2(IK,J)-C2(IK-1,JC)
119         CONTINUE
120      CONTINUE
         NAC = 1
         IF (IDO .EQ. 2) RETURN
         NAC = 0
         DO 121 IK=1,IDL1
            C2(IK,1) = CH2(IK,1)
121      CONTINUE
         DO 123 J=2,IP
            DO 122 K=1,L1
               C1(1,K,J) = CH(1,K,J)
               C1(2,K,J) = CH(2,K,J)
122         CONTINUE
123      CONTINUE
         IF (IDOT .GT. L1) GO TO 127
         IDIJ = 0
         DO 126 J=2,IP
            IDIJ = IDIJ+2
            DO 125 I=4,IDO,2
               IDIJ = IDIJ+2
               DO 124 K=1,L1
                  C1(I-1,K,J) = WA(IDIJ-1)*CH(I-1,K,J)-WA(IDIJ)*CH(I,K,J)
                  C1(I,K,J) = WA(IDIJ-1)*CH(I,K,J)+WA(IDIJ)*CH(I-1,K,J)
124            CONTINUE
125         CONTINUE
```

```
126 CONTINUE
    RETURN
127 IDJ = 2-IDO
    DO 130 J=2,IP
       IDJ = IDJ+IDO
       DO 129 K=1,L1
          IDIJ = IDJ
          DO 128 I=4,IDO,2
             IDIJ = IDIJ+2
             C1(I-1,K,J) = WA(IDIJ-1)*CH(I-1,K,J)-WA(IDIJ)*CH(I,K,J)
             C1(I,K,J) = WA(IDIJ-1)*CH(I,K,J)+WA(IDIJ)*CH(I-1,K,J)
128       CONTINUE
129    CONTINUE
130 CONTINUE
    RETURN
    END

SUBROUTINE PASSB2 (IDO,L1,CC,CH,WA1)
    DIMENSION       CC(IDO,2,L1)          ,CH(IDO,L1,2)         ,
   1                WA1(1)
    IF (IDO .GT. 2) GO TO 102
    DO 101 K=1,L1
       CH(1,K,1) = CC(1,1,K)+CC(1,2,K)
       CH(1,K,2) = CC(1,1,K)-CC(1,2,K)
       CH(2,K,1) = CC(2,1,K)+CC(2,2,K)
       CH(2,K,2) = CC(2,1,K)-CC(2,2,K)
101 CONTINUE
    RETURN
102 DO 104 K=1,L1
       DO 103 I=2,IDO,2
          CH(I-1,K,1) = CC(I-1,1,K)+CC(I-1,2,K)
          TR2 = CC(I-1,1,K)-CC(I-1,2,K)
          CH(I,K,1) = CC(I,1,K)+CC(I,2,K)
          TI2 = CC(I,1,K)-CC(I,2,K)
          CH(I,K,2) = WA1(I-1)*TI2+WA1(I)*TR2
          CH(I-1,K,2) = WA1(I-1)*TR2-WA1(I)*TI2
103    CONTINUE
104 CONTINUE
    RETURN
    END

SUBROUTINE PASSB3 (IDO,L1,CC,CH,WA1,WA2)
    DIMENSION       CC(IDO,3,L1)          ,CH(IDO,L1,3)         ,
   1                WA1(1)    ,WA2(1)
    DATA TAUR,TAUI /-.5,.866025403784439/
    IF (IDO .NE. 2) GO TO 102
    DO 101 K=1,L1
```

```
              TR2 = CC(1,2,K)+CC(1,3,K)
              CR2 = CC(1,1,K)+TAUR*TR2
              CH(1,K,1) = CC(1,1,K)+TR2
              TI2 = CC(2,2,K)+CC(2,3,K)
              CI2 = CC(2,1,K)+TAUR*TI2
              CH(2,K,1) = CC(2,1,K)+TI2
              CR3 = TAUI*(CC(1,2,K)-CC(1,3,K))
              CI3 = TAUI*(CC(2,2,K)-CC(2,3,K))
              CH(1,K,2) = CR2-CI3
              CH(1,K,3) = CR2+CI3
              CH(2,K,2) = CI2+CR3
              CH(2,K,3) = CI2-CR3
      101 CONTINUE
          RETURN
      102 DO 104 K=1,L1
              DO 103 I=2,IDO,2
                  TR2 = CC(I-1,2,K)+CC(I-1,3,K)
                  CR2 = CC(I-1,1,K)+TAUR*TR2
                  CH(I-1,K,1) = CC(I-1,1,K)+TR2
                  TI2 = CC(I,2,K)+CC(I,3,K)
                  CI2 = CC(I,1,K)+TAUR*TI2
                  CH(I,K,1) = CC(I,1,K)+TI2
                  CR3 = TAUI*(CC(I-1,2,K)-CC(I-1,3,K))
                  CI3 = TAUI*(CC(I,2,K)-CC(I,3,K))
                  DR2 = CR2-CI3
                  DR3 = CR2+CI3
                  DI2 = CI2+CR3
                  DI3 = CI2-CR3
                  CH(I,K,2) = WA1(I-1)*DI2+WA1(I)*DR2
                  CH(I-1,K,2) = WA1(I-1)*DR2-WA1(I)*DI2
                  CH(I,K,3) = WA2(I-1)*DI3+WA2(I)*DR3
                  CH(I-1,K,3) = WA2(I-1)*DR3-WA2(I)*DI3
      103     CONTINUE
      104 CONTINUE
          RETURN
          END

SUBROUTINE PASSB4 (IDO,L1,CC,CH,WA1,WA2,WA3)
          DIMENSION     CC(IDO,4,L1)        ,CH(IDO,L1,4)            ,
         1              WA1(1)     ,WA2(1)      ,WA3(1)
          IF (IDO .NE. 2) GO TO 102
          DO 101 K=1,L1
              TI1 = CC(2,1,K)-CC(2,3,K)
              TI2 = CC(2,1,K)+CC(2,3,K)
              TR4 = CC(2,4,K)-CC(2,2,K)
              TI3 = CC(2,2,K)+CC(2,4,K)
              TR1 = CC(1,1,K)-CC(1,3,K)
              TR2 = CC(1,1,K)+CC(1,3,K)
```

```
              TI4 = CC(1,2,K)-CC(1,4,K)
              TR3 = CC(1,2,K)+CC(1,4,K)
              CH(1,K,1) = TR2+TR3
              CH(1,K,3) = TR2-TR3
              CH(2,K,1) = TI2+TI3
              CH(2,K,3) = TI2-TI3
              CH(1,K,2) = TR1+TR4
              CH(1,K,4) = TR1-TR4
              CH(2,K,2) = TI1+TI4
              CH(2,K,4) = TI1-TI4
  101   CONTINUE
        RETURN
  102   DO 104 K=1,L1
           DO 103 I=2,IDO,2
              TI1 = CC(I,1,K)-CC(I,3,K)
              TI2 = CC(I,1,K)+CC(I,3,K)
              TI3 = CC(I,2,K)+CC(I,4,K)
              TR4 = CC(I,4,K)-CC(I,2,K)
              TR1 = CC(I-1,1,K)-CC(I-1,3,K)
              TR2 = CC(I-1,1,K)+CC(I-1,3,K)
              TI4 = CC(I-1,2,K)-CC(I-1,4,K)
              TR3 = CC(I-1,2,K)+CC(I-1,4,K)
              CH(I-1,K,1) = TR2+TR3
              CR3 = TR2-TR3
              CH(I,K,1) = TI2+TI3
              CI3 = TI2-TI3
              CR2 = TR1+TR4
              CR4 = TR1-TR4
              CI2 = TI1+TI4
              CI4 = TI1-TI4
              CH(I-1,K,2) = WA1(I-1)*CR2-WA1(I)*CI2
              CH(I,K,2) = WA1(I-1)*CI2+WA1(I)*CR2
              CH(I-1,K,3) = WA2(I-1)*CR3-WA2(I)*CI3
              CH(I,K,3) = WA2(I-1)*CI3+WA2(I)*CR3
              CH(I-1,K,4) = WA3(I-1)*CR4-WA3(I)*CI4
              CH(I,K,4) = WA3(I-1)*CI4+WA3(I)*CR4
  103      CONTINUE
  104   CONTINUE
        RETURN
        END

SUBROUTINE PASSB5 (IDO,L1,CC,CH,WA1,WA2,WA3,WA4)
        DIMENSION      CC(IDO,5,L1)        ,CH(IDO,L1,5)
       1               WA1(1)      ,WA2(1)      ,WA3(1)      ,WA4(1)
        DATA TR11,TI11,TR12,TI12 /.309016994374947,.951056516295154,
       1-.809016994374947,.587785252292473/
        IF (IDO .NE. 2) GO TO 102
        DO 101 K=1,L1
```

```
              TI5 = CC(2,2,K)-CC(2,5,K)
              TI2 = CC(2,2,K)+CC(2,5,K)
              TI4 = CC(2,3,K)-CC(2,4,K)
              TI3 = CC(2,3,K)+CC(2,4,K)
              TR5 = CC(1,2,K)-CC(1,5,K)
              TR2 = CC(1,2,K)+CC(1,5,K)
              TR4 = CC(1,3,K)-CC(1,4,K)
              TR3 = CC(1,3,K)+CC(1,4,K)
              CH(1,K,1) = CC(1,1,K)+TR2+TR3
              CH(2,K,1) = CC(2,1,K)+TI2+TI3
              CR2 = CC(1,1,K)+TR11*TR2+TR12*TR3
              CI2 = CC(2,1,K)+TR11*TI2+TR12*TI3
              CR3 = CC(1,1,K)+TR12*TR2+TR11*TR3
              CI3 = CC(2,1,K)+TR12*TI2+TR11*TI3
              CR5 = TI11*TR5+TI12*TR4
              CI5 = TI11*TI5+TI12*TI4
              CR4 = TI12*TR5-TI11*TR4
              CI4 = TI12*TI5-TI11*TI4
              CH(1,K,2) = CR2-CI5
              CH(1,K,5) = CR2+CI5
              CH(2,K,2) = CI2+CR5
              CH(2,K,3) = CI3+CR4
              CH(1,K,3) = CR3-CI4
              CH(1,K,4) = CR3+CI4
              CH(2,K,4) = CI3-CR4
              CH(2,K,5) = CI2-CR5
       101 CONTINUE
           RETURN
       102 DO 104 K=1,L1
              DO 103 I=2,IDO,2
                 TI5 = CC(I,2,K)-CC(I,5,K)
                 TI2 = CC(I,2,K)+CC(I,5,K)
                 TI4 = CC(I,3,K)-CC(I,4,K)
                 TI3 = CC(I,3,K)+CC(I,4,K)
                 TR5 = CC(I-1,2,K)-CC(I-1,5,K)
                 TR2 = CC(I-1,2,K)+CC(I-1,5,K)
                 TR4 = CC(I-1,3,K)-CC(I-1,4,K)
                 TR3 = CC(I-1,3,K)+CC(I-1,4,K)
                 CH(I-1,K,1) = CC(I-1,1,K)+TR2+TR3
                 CH(I,K,1) = CC(I,1,K)+TI2+TI3
                 CR2 = CC(I-1,1,K)+TR11*TR2+TR12*TR3
                 CI2 = CC(I,1,K)+TR11*TI2+TR12*TI3
                 CR3 = CC(I-1,1,K)+TR12*TR2+TR11*TR3
                 CI3 = CC(I,1,K)+TR12*TI2+TR11*TI3
                 CR5 = TI11*TR5+TI12*TR4
                 CI5 = TI11*TI5+TI12*TI4
                 CR4 = TI12*TR5-TI11*TR4
                 CI4 = TI12*TI5-TI11*TI4
                 DR3 = CR3-CI4
```

```
              DR4 = CR3+CI4
              DI3 = CI3+CR4
              DI4 = CI3-CR4
              DR5 = CR2+CI5
              DR2 = CR2-CI5
              DI5 = CI2-CR5
              DI2 = CI2+CR5
              CH(I-1,K,2) = WA1(I-1)*DR2-WA1(I)*DI2
              CH(I,K,2)   = WA1(I-1)*DI2+WA1(I)*DR2
              CH(I-1,K,3) = WA2(I-1)*DR3-WA2(I)*DI3
              CH(I,K,3)   = WA2(I-1)*DI3+WA2(I)*DR3
              CH(I-1,K,4) = WA3(I-1)*DR4-WA3(I)*DI4
              CH(I,K,4)   = WA3(I-1)*DI4+WA3(I)*DR4
              CH(I-1,K,5) = WA4(I-1)*DR5-WA4(I)*DI5
              CH(I,K,5)   = WA4(I-1)*DI5+WA4(I)*DR5
       103    CONTINUE
       104 CONTINUE
           RETURN
           END
```

Obviously, other modifications and variations of the present invention may be possible in light of the foregoing teachings. It is therefore to be understood that within the scope of the appended claims the invention may be practiced otherwise than as specifically described.

What is claimed is:

1. A method of determining the thermal conductivity of a fiber comprising the steps of:

A. suspending a cylindrical sample fiber selected from the group consisting of metal fibers and graphite fibers in a working fluid having a high refractive index change with temperature;

B. heating the sample fiber at a first point by means of a pump laser beam that is modulated at a frequency of less than 200 hertz;

C. passing a weak continuous intensity probe laser beam through the working fluid close to a second point on the sample fiber so that a deflection of the probe beam occurs that is a measure of the amplitude and phase shift of a synchronous thermal wave passing through the second point as a result of the heating of the sample fiber by the modulated pump laser beam;

D. converting the probe laser beam deflection into an electrical signal whose amplitude and phase shift correspond to the amplitude and phase shift of the synchronous thermal wave as it passes through the second point on the sample fiber;

E. recording either the maximum or the RMS amplitude of the electrical signal and the corresponding distance between the first point and the second point on the sample fiber;

F. changing the distance between the first point and the second point on the sample fiber and repeating steps B through E and continuing this procedure until the amplitude of the electrical signal has been measured at a desired number of different distances between the first point and the second point on the sample fiber;

G. determining the straight line slope of a plot of the logarithm of the amplitude of the electrical signal versus the distance between the first point and the second point on the sample fiber;

H. using a mathematical model for the synchronous thermal wave produced in a theoretical uniform cylindrical fiber by a modulated pump laser beam heat source at a first point to calculate the maximum theoretical amplitude of the thermal wave for each of a series of second points along the theoretical uniform cylindrical fiber from inputs which include the modulation frequency of the real pump laser beam used to heat the sample fiber in step B, the actual density, specific heat, and diameter of the sample fiber, the distance of each second point from the first point, on the theoretical fiber, and an initial estimate of the thermal conductivity of the sample fiber which is to be determined;

I. finding the straight line slope of a plot of the logarithm of the maximum theoretical amplitude of the mathematical model thermal wave at each second point on the theoretical fiber versus the distance of the second point from the first point on the theoretical fiber;

J. comparing the straight line slope of the logarithm of the calculated maximum theoretical amplitude of the mathematical model thermal wave versus the distance between the first point and the second point on the theoretical fiber (step I) with the straight line slope of the logarithm of the amplitude of the electrical signal versus the distance between the first point and the second point on the sample fiber (step G) and then adjusting the value of the estimated thermal conductivity to bring the slopes closer together; and K. repeating steps H through J until the straight line slope of the logarithm of the calculated maximum theoretical amplitude of the mathematical model thermal wave versus the distance between the first point and the second point on the theoretical fiber is the same as the straight line slope of the logarithm of the amplitude of the electrical signal versus the distance between the first point and the second point on the sample fiber, and the value of thermal conductivity last used is the correct one.

2. The method of claim 1 wherein the pump laser beam is perpendicular to the axis of the sample fiber and the probe laser beam is perpendicular to the axis of the sample fiber and to the pump laser beam.

3. The method of claim 1 wherein the pump laser beam is modulated at a frequency of from 20 to less than 200 Hz.

4. The method of claim 1 wherein the fiber has a diameter of from 5 to 100 µm.

5. The method of claim 1 wherein the sample fiber is a graphite fiber.

6. The method of claim 1 wherein the thermal conductivity of the sample fiber is greater than 100 W/m-K.

7. A method of determining the thermal conductivity of a fiber comprising the steps of:

A. suspending a cylindrical sample fiber selected from the group consisting of metal fibers and graphite fibers in a working fluid having a high refractive index change with temperature;

B. heating the sample fiber at a first point by means of a pump laser beam that is modulated at a frequency of less than 200 hertz;

C. passing a weak continuous intensity probe laser beam through the working fluid close to a second point on the sample fiber so that a deflection of the probe beam occurs that is a measure of the amplitude and phase shift of a synchronous thermal wave passing through the second point as a result of the heating or the sample fiber by the modulated pump laser beam;

D. converting the probe laser beam deflection into an electrical signal whose amplitude and phase shift correspond to the amplitude and phase shift of the synchronous thermal wave as it passes through the second point on the sample fiber;

E. recording the phase shift of the electrical signal and the corresponding distance between the first point and the second point on the sample fiber;

F. changing the distance between the first point and the second point on the sample fiber and repeating steps B through E and continuing this procedure until the phase shift of the electrical signal has been measured at a desired number of different distances between the first point and the second point on the sample fiber;

G. determining the straight line slope of a plot of the phase shift of the electrical signal versus the distance between the first point and the second point on the sample fiber;

H. using a mathematical model for the synchronous thermal wave produced in a theoretical uniform cylindrical fiber by a modulated pump laser beam heat source at a first point to calculate the theoretical phase shift of the thermal wave for each of a series of second points along the theoretical uniform cylindrical fiber from inputs which include the modulation frequency of the real pump laser beam used to heat the sample fiber in step B, the actual density, specific heat, and diameter of the sample fiber, the distance of each second point from the first point on the theoretical fiber, and an initial estimate of the thermal conductivity of the sample fiber which is to be determined;

I. finding the straight line slope of a plot of the theoretical phase shift of the mathematical model thermal wave at each second point on the theoretical fiber versus the distance of the second point from the first point on the theoretical fiber;

J. comparing the straight line slope of the calculated phase shift of the mathematical model thermal wave versus the distance between the first point and the second point on the theoretical fiber (step I) with the straight line slope of the phase shift of the electrical signal versus the distance between the first point and the second point on the sample fiber (step G) and then adjusting the value of the estimated thermal conductivity to bring the slopes closer together; and K. repeating steps H through J until the straight line slope of the calculated phase shift of the mathematical model thermal wave versus the distance between the first point and the second point on the theoretical fiber is from same as the straight line slope of the phase shift of the electrical signal versus the distance between the first point and the second point on the sample fiber, and the value of thermal conductivity last used is the correct one.

8. The method of claim 7 wherein the pump laser beam is perpendicular to the axis of the sample fiber and the probe laser beam is perpendicular to the axis of the sample fiber and to the pump laser beam.

9. The method of claim 7 wherein the pump laser beam is modulated at a frequency of from 20 to less than 200 Hz.

10. The method of claim 7 wherein the fiber has a diameter of from 5 to 100 µm.

11. The method of claim 7 wherein the sample fiber is a graphite fiber.

12. The method of claim 7 wherein the thermal conductivity of the sample fiber is greater than 100 W/m-K.

13. A method of determining the thermal conductivity of a fiber comprising the steps of:

A. suspending a cylindrical sample fiber selected from the group consisting of metal fibers and graphite fibers in a working fluid having a high refractive index change with temperature;

B. heating the sample fiber at a first point by means of a pump laser beam that is modulated at a frequency of less than 200 hertz;

C. passing a weak continuous intensity probe laser beam through the working fluid close to a second point on the sample fiber so that a deflection of the probe beam occurs that is a measure of the amplitude and phase shift of a synchronous thermal wave passing through the second point as a result of the heating of the sample fiber by the modulated pump laser beam;

D. converting the probe laser beam deflection into an electrical signal whose amplitude and phase shift correspond to the amplitude and phase shift of the synchronous thermal wave as it passes through the second point on the sample fiber;

E. recording (1) the phase shift of the electrical signal, (2) either the maximum or the RMS amplitude of the electrical signal, and (3) the corresponding distance between the first point and the second point on the sample fiber;

F. changing the distance between the first point and the second point on the sample fiber and repeating steps B through E and continuing this procedure until both the phase shift of the electrical signal and the amplitude of the electrical signal have been measured at a desired number of different distances between the first point and the second point on the sample fiber;

G. determining the straight line slope of a plot of the phase shift of the electrical signal versus the distance between the first point and the second point on the sample fiber and also determining the straight line slope of a plot of the logarithm of the amplitude of the electrical signal versus the distance between the first point and the second point on the sample fiber;

H. using a mathematical model for the synchronous thermal wave produced in a theoretical uniform cylindrical fiber by a modulated pump laser beam heat source at a first point to calculate the theoretical phase shift of the thermal wave for each of a series of second points along the theoretical uniform cylindrical fiber from inputs which include the modulation frequency of the real pump laser beam used to heat the sample fiber in step B, the actual density, specific heat, and diameter of the sample fiber, the distance of each second point from the first point on the theoretical fiber, and an initial estimate of the thermal conductivity of the sample fiber which is to be determined;

I. finding the straight line slope of a plot of the theoretical phase shift of the mathematical model thermal wave at each second point on the theoretical fiber versus the distance of the second point from the first point on the theoretical fiber;

J. comparing the straight line slope of the calculated phase shift of the mathematical model thermal wave versus the distance between the first, point and the second point on the theoretical fiber (step I) with the straight line slope of the phase shift of the electrical signal versus the distance between the first point and the second point on the sample fiber (step G) and then adjusting the value of the estimated thermal conductivity to bring the slopes closer together;

K. repeating steps H through J until the straight line slope of the calculated phase shift of the mathematical model thermal wave versus the distance between the first point and the second point on the theoretical fiber is the same as the straight line slope of the phase shift of the electrical signal versus the distance between the first point and the second point on the sample fiber, and the value of thermal conductivity last used is the thermal conductivity determine by phase shift;

L. using the mathematical model of step H for the synchronous thermal wave produced in the theoretical uniform cylindrical fiber by the pump laser beam heat source at a first point to calculate the theoretical amplitude of the thermal wave for each of a series of second points along the theoretical uniform cylindrical fiber;

M. finding the straight line slope of a plot of the logarithm of the theoretical amplitude of the mathematical model thermal wave at each second point on the theoretical fiber versus the distance of the second point from the first point on the theoretical fiber;

N. comparing the straight line slope of the logarithm of the calculated theoretical amplitude of the mathematical model thermal wave versus the distance between the first point and the second point on the theoretical fiber (step M) with the straight line slope of the logarithm of the amplitude of the electrical signal versus the distance between the first point and the second point on the sample fiber (step G) and then adjusting the value of the estimated thermal conductivity to bring the slopes closer together; and O. repeating steps L through N until the straight line slope of the logarithm of the calculated theoretical amplitude of the mathematical model thermal wave versus the distance between the first point and the second point on the theoretical fiber is same as the straight line slope of the logarithm of the amplitude of the electrical signal versus the distance between the first point and the second point on the sample fiber, and the value of thermal conductivity last used is the thermal conductivity determined by amplitude; and P. comparing the thermoconductivity determined by amplitude with the thermoconductivity determined by phase shift where close agreement indicates an accurate result.

14. The method of claim 13 wherein the pump laser beam is perpendicular to the axis of the sample fiber and the probe laser beam is perpendicular to the axis of the sample fiber and to the pump laser beam.

15. The method of claim 13 wherein the pump laser beam is modulated at a frequency of from 20 to less than 200 Hz.

16. The method of claim 13 wherein the diameter of the cylindrical sample fiber is from 5 to 100 µm.

17. The method of claim 13 wherein the sample fiber is a graphite fiber.

18. The method of claim 13 wherein the thermal conductivity of the sample fiber is greater than 100 w/m-K.

* * * * *